(12) United States Patent
Osypka et al.

(10) Patent No.: US 11,357,451 B2
(45) Date of Patent: Jun. 14, 2022

(54) INTRAVASCULAR MAPPING CATHETER WITH IRRIGATED BASKET ASSEMBLY

(71) Applicant: Oscor Inc., Palm Harbor, FL (US)

(72) Inventors: Thomas P. Osypka, Palm Harbor, FL (US); Timothy Searfoss, New Port Richey, FL (US); Allan Fuentes, Spring Hills, FL (US)

(73) Assignee: Oscor Inc., Palm Harbor, FL (US)

( * ) Notice: Subject to any disclaimer, the term of this patent is extended or adjusted under 35 U.S.C. 154(b) by 301 days.

(21) Appl. No.: 16/214,608

(22) Filed: Dec. 10, 2018

(65) Prior Publication Data

US 2020/0178897 A1 Jun. 11, 2020

(51) Int. Cl.
| | | |
|---|---|---|
| *A61B 5/05* | (2021.01) | |
| *A61B 18/18* | (2006.01) | |
| *A61B 5/00* | (2006.01) | |
| *A61L 29/02* | (2006.01) | |
| *A61B 5/287* | (2021.01) | |

(52) U.S. Cl.
CPC ............ *A61B 5/6858* (2013.01); *A61B 5/287* (2021.01); *A61L 29/02* (2013.01); *A61B 2217/007* (2013.01); *A61B 2562/0209* (2013.01)

(58) Field of Classification Search
CPC .............. A61B 5/0422; A61B 18/1492; A61B 2018/00214; A61B 2018/00267; A61B 5/287; A61B 2018/00577; A61B 2018/0016; A61B 5/6858; A61B 2218/002; A61B 2018/00011; A61B 2018/0022; A61B 2018/1465; A61B 2017/22038; A61B 2018/00232; A61B 5/6859; A61B 18/02; A61B 2017/00243; A61B 2018/00285; A61B 2018/1467; A61B 2017/00053; A61B 2018/00351
USPC ................ 600/372–374, 377, 393, 434–435, 600/508–509; 606/20–26; 607/115, 607/119–123
See application file for complete search history.

(56) References Cited

U.S. PATENT DOCUMENTS

| | | | |
|---|---|---|---|
| 5,279,299 A | 1/1994 | Imran | |
| 5,624,392 A * | 4/1997 | Saab ................. | A61M 25/1029 604/113 |
| 5,628,313 A | 5/1997 | Webster, Jr. | |
| 5,647,870 A * | 7/1997 | Kordis ................... | A61B 5/287 606/41 |
| 6,280,414 B1 | 8/2001 | Shah et al. | |
| 7,955,299 B2 | 6/2011 | Just et al. | |

(Continued)

*Primary Examiner* — Joseph A Stoklosa
*Assistant Examiner* — Brian M Antiskay
(74) *Attorney, Agent, or Firm* — Locke Lord LLP; Scott D. Wofsy (57) ABSTRACT

An intravascular catheter system for cardiac mapping is disclosed which includes a housing having opposed proximal and distal portions, an elongated catheter shaft operatively associated with the distal portion of the housing, an elongated electrical conduit operatively associated with the proximal portion of the housing and an elongated irrigation conduit operatively associated with the proximal portion of the housing, wherein an irrigated basket assembly is operatively associated with a distal end portion of the catheter shaft and it includes a plurality of circumferentially arranged electrically insulated tubular splines each having a plurality of longitudinally spaced apart mapping electrodes thereon.

12 Claims, 5 Drawing Sheets

(56) References Cited

U.S. PATENT DOCUMENTS

| | | | |
|---|---|---|---|
| 8,825,130 B2 | 9/2014 | Just et al. | |
| 8,961,509 B2 * | 2/2015 | Falwell | A61B 5/0422 |
| | | | 604/95.04 |
| 8,979,839 B2 * | 3/2015 | De La Rama | A61B 18/1492 |
| | | | 606/41 |
| 9,339,331 B2 * | 5/2016 | Tegg | A61B 18/1492 |
| 9,687,297 B2 * | 6/2017 | Just | A61B 5/0422 |
| 9,693,733 B2 * | 7/2017 | Altmann | A61M 25/0147 |
| 9,848,795 B2 * | 12/2017 | Marecki | A61B 5/6858 |
| 10,362,991 B2 * | 7/2019 | Tran | A61B 5/287 |
| 2013/0274582 A1 * | 10/2013 | Afonso | A61B 5/6852 |
| | | | 600/374 |
| 2013/0304047 A1 * | 11/2013 | Grunewald | A61B 18/1815 |
| | | | 606/14 |
| 2017/0065227 A1 * | 3/2017 | Marrs | A61B 5/6858 |

\* cited by examiner

INTRAVASCULAR MAPPING CATHETER WITH IRRIGATED BASKET ASSEMBLY

BACKGROUND OF THE INVENTION

1. Field of the Invention

The subject invention is directed to an intravascular catheter, and more particularly, to a cardiac mapping catheter having an irrigated basket-shaped electrode assembly.

2. Description of Related Art

Cardiac arrhythmias are a leading cause of stroke, heart disease, and sudden death. The physiological mechanism of arrhythmia involves an abnormality in the electrical conduction of the heart. There are a number of treatment options for patients with arrhythmia that include medication, implantable devices, and catheter ablation of cardiac tissue.

Traditionally, the arrhythmia is studied and diagnosed by "electrically mapping" the heart with catheters inserted through the vasculature into a heart chamber. For example, mapping catheters are known from U.S. Pat. No. 5,628,313 to Webster, which describes a basket catheter. In use, this flexible and conformal catheter is deployed in the heart and presses individual electrodes against the chamber wall for full chamber contact mapping of a beating heart.

Smaller multiple electrode catheters are known as well. For example, the U.S. Pat. No. 5,279,299 to Imran illustrates techniques for creating smaller catheter arrays that are used to selectively contact map portions of a cardiac chamber. This catheter is flexible and the electrodes remain in contact with the chamber wall even when the catheter shaft is displaced slightly. In each of these examples, the limbs of the catheter are very flexible and gently contact the chamber wall while the wall of the heart is moving.

Although such cardiac mapping methods are known in the art and various deflectable, displaceable and deployable catheters are known as well, there is a common negative clinical side effects of such multi-array and multi-spine catheters, in that such complex configurations, while exposed for a prolonged time inside the blood stream, have a strong tendency to collect blood in the areas of high mechanical complexity and with that show a high risk of coagulation.

There is a clinical need to have a multi-array, multi-spine cardiac mapping catheter, while at the same time have a means to prevent coagulation while inserted into the cardiovascular system and heart chambers, and improve the accuracy, stability and maneuverability of such devices, so that they can be more widely used, especially as an adjunct to cardiac ablation procedures. The subject invention meets this clinical need by providing a mapping catheter having an irrigated basket-shaped electrode assembly that reduces the risk of coagulation and thromboses during a prolonged cardiac mapping procedure.

SUMMARY OF THE DISCLOSURE

The subject invention is directed to a new and useful intravascular catheter system for cardiac mapping. The system includes a central housing having opposed proximal and distal end portions, an elongated catheter shaft operatively associated with the distal end portion of the housing, an elongated electrical conduit operatively associated with the proximal end portion of the housing and an elongated irrigation conduit operatively associated with the end proximal portion of the housing.

The catheter shaft has an elongated central support wire extending therethrough and an irrigated basket assembly is operatively associated with a distal end portion of the catheter shaft. The irrigated basket assembly has opposed proximal and distal portions and includes a plurality of circumferentially arranged electrically insulated tubular splines. Each of the tubular splines in the irrigated basket assembly has a plurality of longitudinally spaced apart mapping electrodes provided thereon.

The irrigated basket assembly is adapted and configured to transition between a first position and a second position. In the first position, the tubular splines of the basket assembly are compressed radially inwardly toward the central support wire for insertion and delivery into the vasculature of a patient. In the second position, the tubular splines of the basket assembly are spread radially outwardly away from the central support wire for physiological mapping.

The irrigated basket assembly includes at least four circumferentially arranged tubular splines. In one embodiment of the subject invention, the irrigated basket assembly has four (4) circumferentially arranged tubular splines. In another embodiment of the subject invention, the irrigated basket assembly has six (6) circumferentially arranged tubular splines. Preferably, each of the circumferentially arranged splines has at least three (3) spaced apart generally cylindrical mapping electrodes thereon.

The electrical conduit supports a plurality of electrical conductors that extend through the catheter shaft and into the tubular splines of the basket assembly for communicating with the plurality of spaced apart mapping electrodes. The electrical conduit has an electrical connector operatively associated with a proximal end thereof for communicating with a power source.

The irrigation conduit supports an elongated irrigation lumen that extends through the catheter shaft and surrounds the central support wire so as to define an irrigation gap therebetween. The irrigation conduit has an irrigation port assembly operatively associated with a proximal end portion thereof for communicating with a fluid source.

The irrigation lumen has an open distal end adjacent the distal end portion of the basket assembly. The open distal end of the irrigation lumen allows for the egress of irrigation fluid from the irrigation gap. The irrigation lumen also includes at least one weeping hole or port adjacent the proximal end portion of the basket assembly to allow for the egress of irrigation fluid from the irrigation gap.

An elongated sprocket is provided in the distal end portion of the catheter shaft, adjacent the proximal end portion of the irrigated basket assembly. The sprocket has a number of circumferentially spaced apart outer grooves formed therein for maintaining the plurality of electrical conductors in a number of circumferentially spaced apart groups corresponding to the number of tubular splines. The elongated sprocket also has a central bore extending therethrough for accommodating the central support wire and the irrigation lumen in a coaxial manner.

Preferably, each of the tubular splines of the irrigated basket assembly has an internal support wire located therein constructed from a shape memory alloy and having an arcuate configuration in the radially outwardly spread condition. The internal support wire in each tubular spline preferably has a generally rectangular cross-section to prevent twisting and maintain radial alignment of the splines.

Each of the mapping electrodes is constructed from an electrically conductive biocompatible material selected from the group of materials group consisting of platinum, platinum iridium alloy, MP35N and stainless steel. Each of the mapping electrodes has a raised circumferential outer surface and wherein ramps are provided at opposed ends of each mapping electrode to provide a smooth transition between an outer surface of the spline and the outer surface of the electrode.

These and other features of the intravascular catheter system of the subject invention will become more readily apparent to those having ordinary skill in the art to which the subject invention appertains from the detailed description of the preferred embodiments taken in conjunction with the following brief description of the drawings.

BRIEF DESCRIPTION OF THE DRAWINGS

So that those skilled in the art will readily understand how to make and use the intravascular catheter system of the subject invention without undue experimentation, preferred embodiments thereof will be described in detail herein below with reference to the figures wherein.

DETAILED DESCRIPTION OF THE PREFERRED EMBODIMENTS

Figure 1:
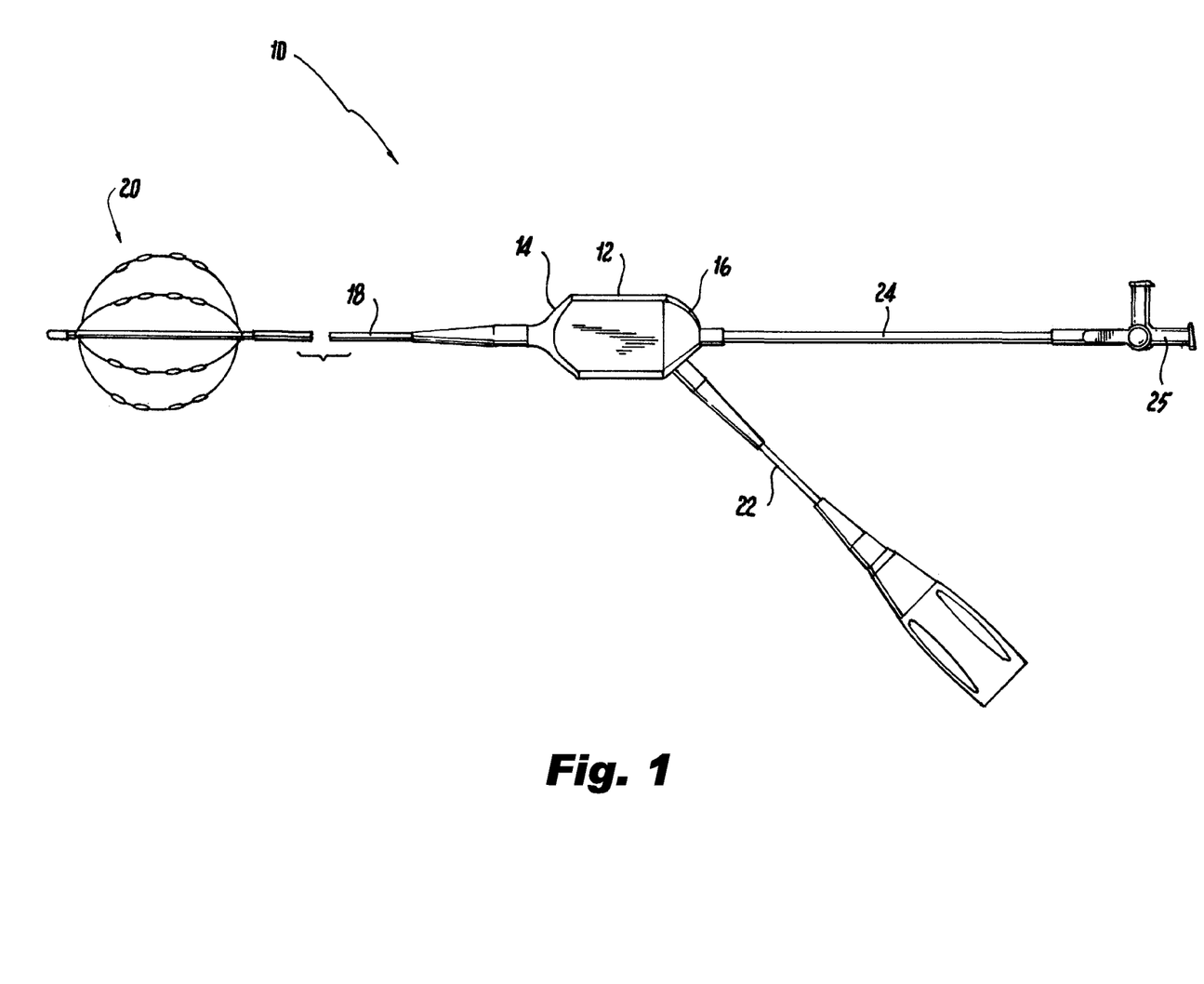
FIG. 1 is side elevational view of the intravascular catheter system of the subject invention with a four-splined irrigated basket assembly in a deployed position.

Referring now to the drawings wherein like reference numeral identify similar structural elements or features of the subject invention, there is illustrated in FIG. 1 a new and useful intravascular catheter system for cardiac mapping, which is designated generally by reference numeral 10. The intravascular catheter system 10 of the subject invention is an electrophysiology catheter designed for deployment within a heart chamber to map electro-anatomical characteristics of the heart and/or to locate and position other catheters within the heart.

Referring now to FIG. 1, the catheter system 10 of the subject invention includes a central housing 12 having opposed distal and proximal end portions 14 and 16. An elongated braided catheter shaft 18 is operatively associated with the distal end portion 14 of the housing 12. An irrigated basket-shaped mapping assembly 20 is operatively associated with a distal end portion of the catheter shaft 18.

In FIG. 1, the basket assembly 20 is a shown as a four-splined assembly. It should be understood however, that the basket assembly associated with catheter system 10 of the subject invention can have more than four splines. Indeed, a six-splined basket assembly is also disclosed herein and it will be described in more detail below with reference to FIG. 5. Both of the basket assemblies disclosed herein are irrigated and constructed in a similar manner.

With continuing reference to FIG. 1, an elongated electrical conduit 22 is operatively associated with the proximal end portion 16 of the central housing 12 and an elongated irrigation conduit 24 is also operatively associated with the proximal end portion 16 of the central housing 12. The catheter shaft 18, irrigated basket assembly 20, electrical conduit 22 and irrigation conduit 24 will be described in greater detail below.

Figure 2:
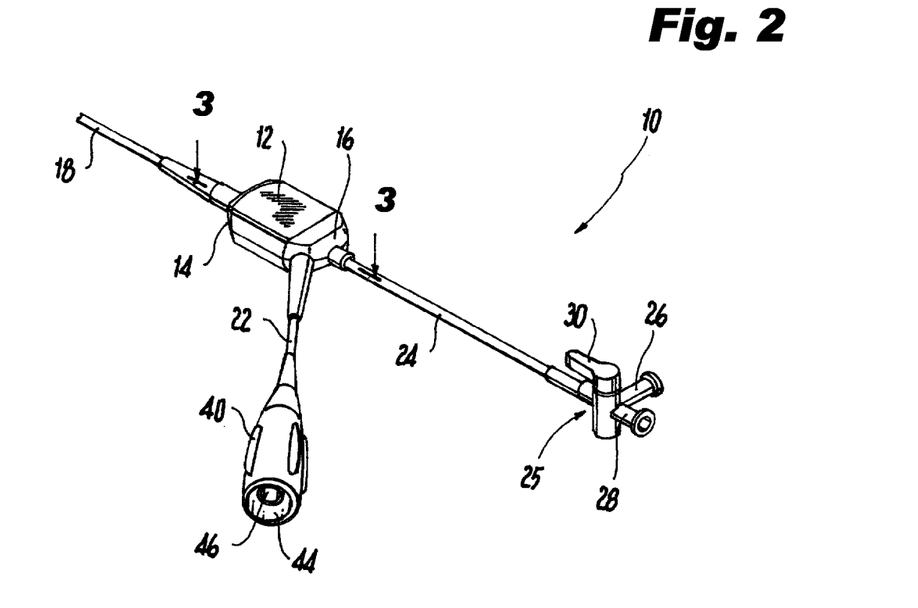
FIG. 2 is perspective view of the proximal end portion of the intravascular catheter system of the subject invention.

Referring to FIG. 2, the irrigation conduit 24 of catheter system 10 has an irrigation port assembly 25 that is operatively associated with a proximal end portion thereof. The irrigation port assembly 25 includes a first connector port 26 for connecting with a first irrigation source, a second connector port 28 for connecting with a second irrigation source, and a three-position toggle valve 30. The connector ports 26 and 28 are preferably conventional luer-type fittings.

The three-position toggle valve 30 is adapted and configured for manual movement between a first position in which the first connector port 26 is open and the second connector port 28 is closed, a second portion in which the first connector port 26 is closed and the second connector port 28 is open, and a third position in which the first connector port 26 and the second connector port 28 are both closed.

Figure 3:
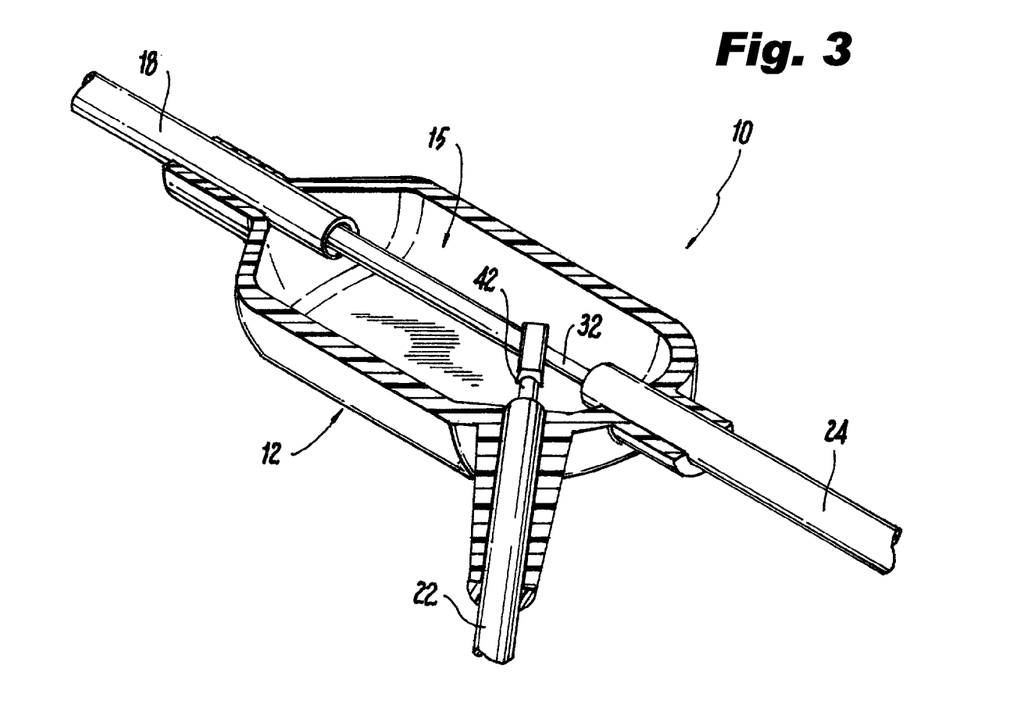
FIG. 3 is an enlarged perspective view in cross-section of the central housing portion of the intravascular catheter system of the subject invention illustrating the conductive wires and irrigation lumen that extend therethrough.

Referring to FIG. 3, an elongated irrigation lumen 32 extends through the irrigation conduit 24 from the irrigation port assembly 25, through the interior cavity 15 of the central housing 12 and into the catheter shaft 18. The irrigation lumen 32 carries fluids (e.g., saline solution or an anti-thrombotic drug or agent) from the irrigation port assembly 25 to the irrigated basket assembly 20 at the distal end of the catheter shaft 18, as discussed in more detail below.

With continuing reference to FIGS. 2 and 3, the electrical conduit 22 of catheter system 10 includes a proximal socket housing 40 that supports a plurality of electrical conductors 42 in a manner for ready connection with an electrical power source. More particularly, as best seen in FIG. 2, the socket housing 40 includes a reception port 44 containing a multi-pin connector 46 that communicates with the electrical conductors 24. The electrical conductors 42 extend from the socket housing 40, through the electrical conduit 22, and into the interior cavity 15 of the central housing 12. From there, the electrical conductors 24 enter the proximal end of the catheter shaft 18 and extend to the basket assembly 20 at the distal end of the catheter shaft 18.

Figure 4:
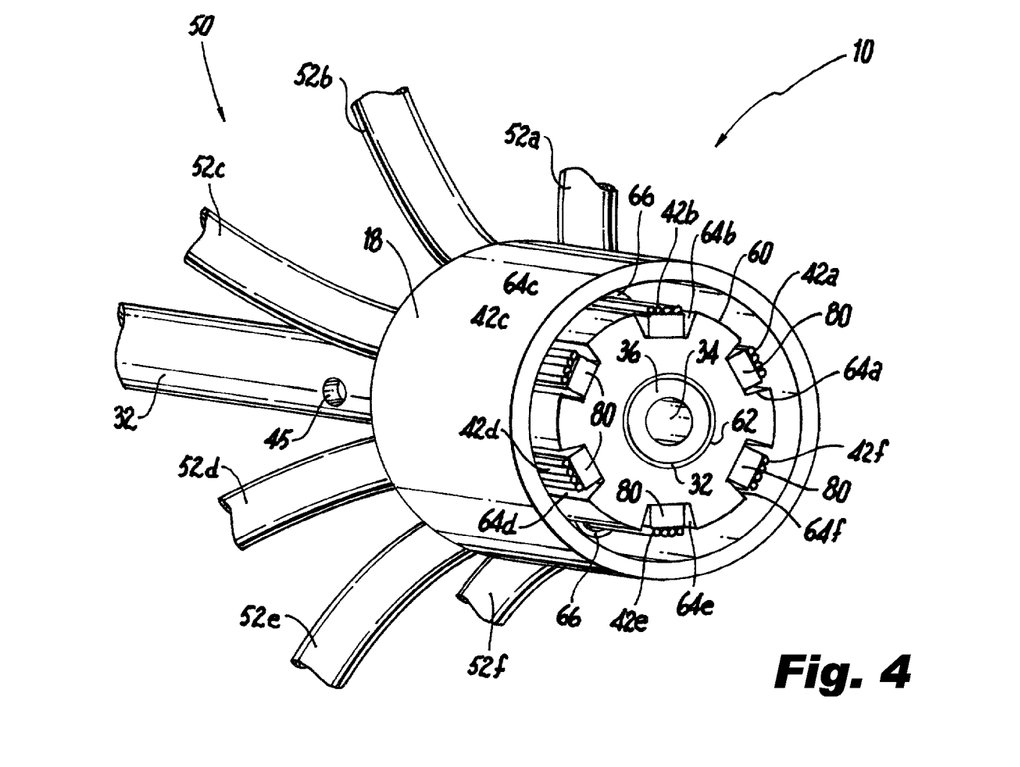
FIG. 4 is an enlarged cross-sectional view of the distal end portion of the catheter shaft taken along line 4-4 of FIG. 5 and illustrating the structural features corresponding to a six-splined basket assembly.
Figure 5:
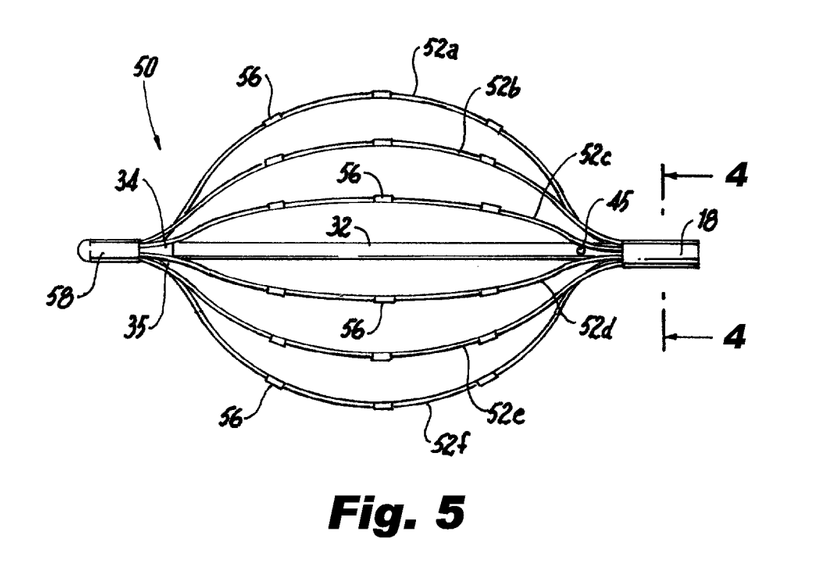
FIG. 5 is a side elevational view of a six-splined irrigated basket assembly constructed in accordance with an embodiment of the subject invention.

Referring now to FIGS. 4 and 5, there is illustrated an irrigated six-splined basket-shaped mapping assembly 50 constructed in accordance with the subject invention. The six-splined basket assembly 50 includes six (6) electrically insulated tubular splines 52a-52f that are supported at their respective distal ends by an atraumatic end cap 58.

Basket assembly 50 is adapted and configured to transition between a first position and a second position. In the first position, the tubular splines 52a-52f are compressed radially inwardly toward the central lumen 32 for intravascular insertion and delivery. In the second position, the tubular splines 52a-52f are spread radially outwardly away from the irrigation lumen 32 to facilitate physiological mapping.

By way of non-limiting example, each spline 52a-52f has at least three (3) longitudinally spaced apart mapping electrodes 56 provided thereon. The mapping electrodes 56 are each associated with a respective electrical conductor 42. In the case of the six-splined basket assembly 50 wherein each of the six (6) splines 52a-52f has four (4) mapping electrodes 56 provided thereon, there are twenty-four (24) electrical conductors 42. As best seen in FIG. 4, these twenty-four (24) electrical conductors 42 are divided into six (6) sets or groups of individually insulated electrical conductors 42a-42f, wherein each set contains four (4) insulated conductors 42.

An elongated cylindrical sprocket 60 formed from a relatively rigid material is provided in the distal end portion of the catheter shaft 18, adjacent to the proximal end portion of the basket assembly, for organizing and effectively separating the components of the catheter assembly 10 that extend therethrough. In particular, the sprocket 60 includes a central bore 62 for coaxially accommodating the irrigation lumen 32 and a central support wire 34 fabricated from Nitinol or a similar material.

More particularly, the central support wire 34 and the irrigation lumen 32 are positioned relative to one another in a coaxial manner so as to form an annular irrigation gap 36 between the outer periphery of the central support wire 34 and the inner periphery of the irrigation lumen 32. The irrigation gap 36 defines a pathway for fluids that are delivered from the irrigation port assembly 25 associated with the irrigation conduit 24 to the six-splined basket assembly 50 at the distal end of catheter shaft 18.

The sprocket 60 further includes six (6) circumferentially spaced apart radially outer grooves 64a-64f for supporting a respective one of the six (6) conductor sets 42a-42f. By supporting and separating the conductors 42 in this manner, the sprocket 60 prevents the conductive wires 42 in each set or group of wires from twisting and kinking as the catheter shaft 18 transits the vasculature of a patient. This effectively reduces the potential for electrical arcing of conductors 42. An arcuate spacer 66 covers each of the six (6) sets of conductors 42a-42f and advantageously maintains spacing between the conductors 42 and the inner wall of the catheter shaft 18.

Figure 6:
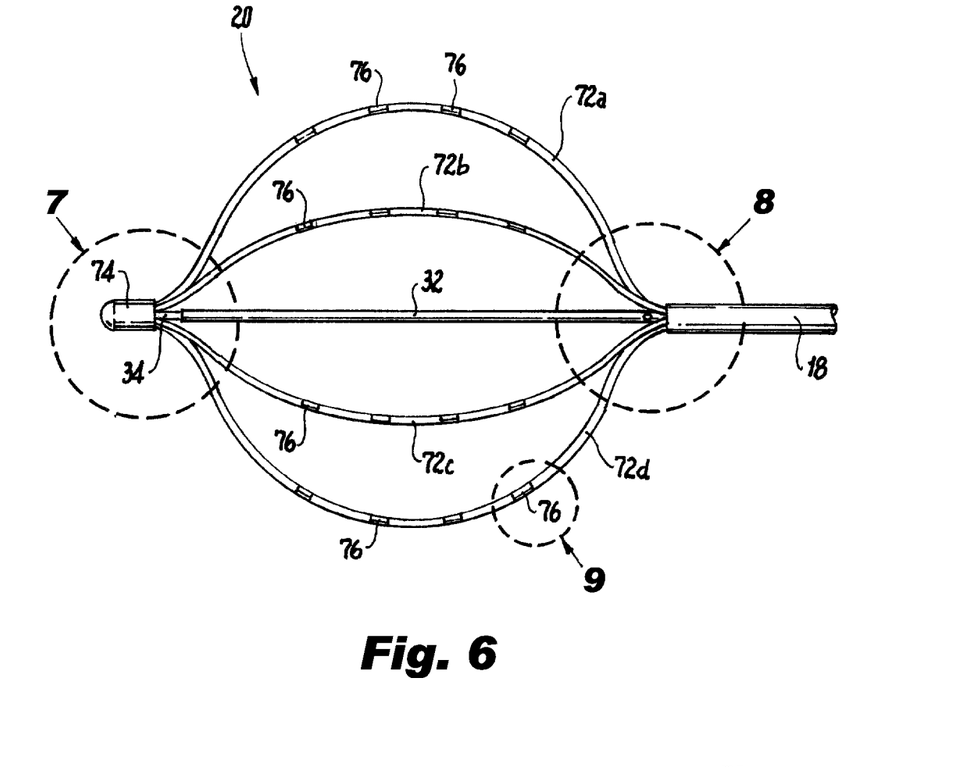
FIG. 6 is a side elevational view of the four-splined irrigated basket assembly illustrated in FIG. 1.
Figure 7:
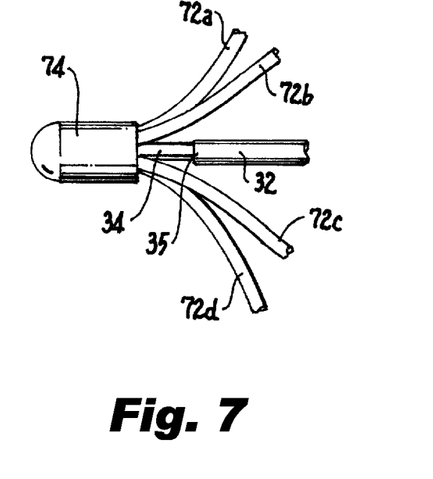
FIG. 7 is an enlarged localized view side elevational view of the distal end portion of the four-splined basket assembly illustrated in FIG. 6, which shows the open distal end of the irrigation gap formed between the central support wire and the irrigation lumen.
Figure 8:
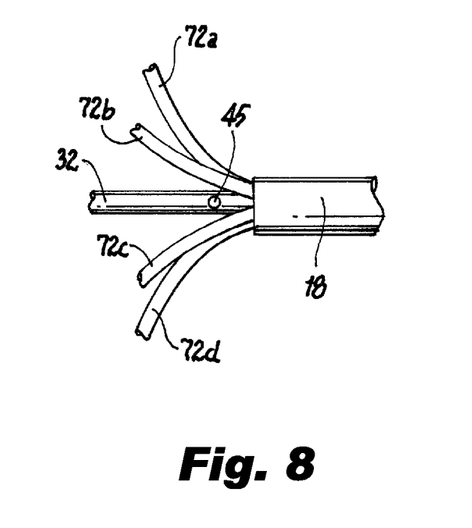
FIG. 8 is an enlarged localized view side elevational view of the proximal end portion of the four-splined basket assembly illustrated in FIG. 6, which shows the weeping holes communicating with the irrigation gap formed between the central support wire and the irrigation lumen.

Referring now to FIGS. 6 through 8, there is illustrated the four-splined irrigated basket assembly 20 previously shown in FIG. 1. In particular, the basket assembly 20 includes four (4) electrically insulated tubular splines 72a-72d that are supported at their respective distal ends by an atraumatic cap 74. Each tubular spline has four (4) longitudinally spaced apart mapping electrodes 76 provided thereon.

The tubular splines 72a-72d are circumferentially arranged around the irrigation lumen 32. The basket assembly 20 is adapted and configured to transition between a first position and a second position. In the first position, the four tubular splines 72a-72d are compressed radially inwardly toward the irrigation lumen 32 for intravascular insertion and delivery. In the second position, the four tubular splines 72a-72d are spread radially outwardly away from the irrigation lumen 32 to facilitate physiological mapping.

As best seen in FIG. 7, the irrigation sleeve 32 has an open distal end 35 adjacent the end cap 74 at the distal portion of the basket assembly 20 to allow for the egress of irrigation fluid from the irrigation gap 36. As best seen in FIG. 8, the irrigation lumen 32 has at least one weeping hole 45 located adjacent the proximal portion of the basket assembly 20 to allow for the egress of irrigation fluid from the irrigation gap 36.

Preferably, there would be a plurality of circumferentially spaced apart weeping holes 45 formed in the wall of the irrigation lumen 32 adjacent the proximal end portion of the basket assembly 20. For example, the irrigation lumen 32 could be formed with four (4) circumferentially spaced apart weeping holes to provide an evenly distributed amount of irrigation fluid. The open distal end 35 and the proximal weeping holes 45 allow the basket assembly 20 to be flushed during the medical mapping procedure using a saline solution or a medicament solution, to prevent thromboses during prolonged mapping procedures. These distal and proximal irrigation features are also provided in the six-splined basket assembly 50 shown in FIGS. 4 and 5.

Figure 9:
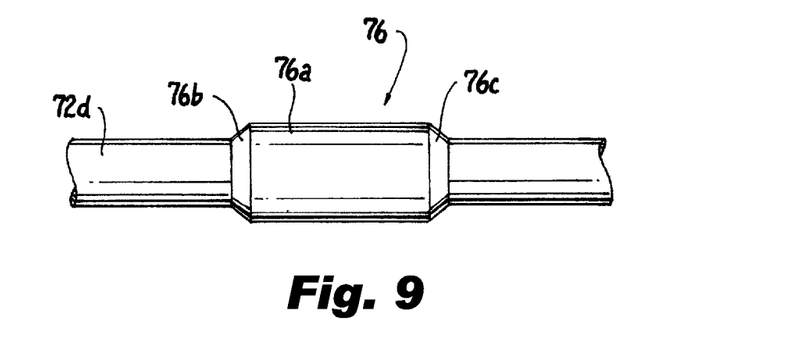
FIG. 9 is an enlarged localized view of a raised mapping electrode as illustrated in FIG. 6.

Referring now to FIG. 9, each mapping electrode (i.e., the mapping electrodes 56 of the six-splined basket assembly 60 and the mapping electrodes 76 of the four-splined basket assembly 20) is constructed from an electrically conductive biocompatible material that is selected from the group of materials consisting of platinum, platinum iridium alloy, MP35N and stainless steel. By way of non-limiting example, mapping electrode 76 has a raised circumferential outer surface 76a with opposed end ramp surfaces 76b and 76c that provide a smooth transition between the outer surface 76a and an outer surface of a cylindrical spline 72d. The raised mapping electrodes provide increased and improved tissue contact while providing smooth transition from spline body, which helps to prevent thromboses along the electrode.

Figure 10:
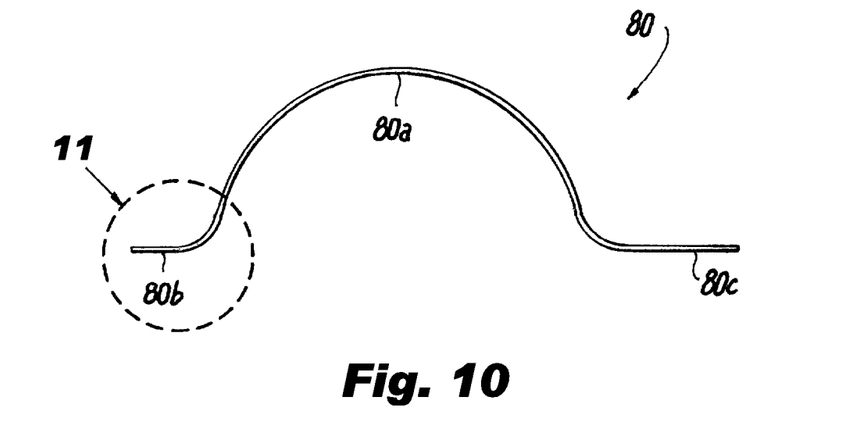
FIG. 10 is a side elevational view of the internal support wire in each spline of the basket assembly.
Figure 11:
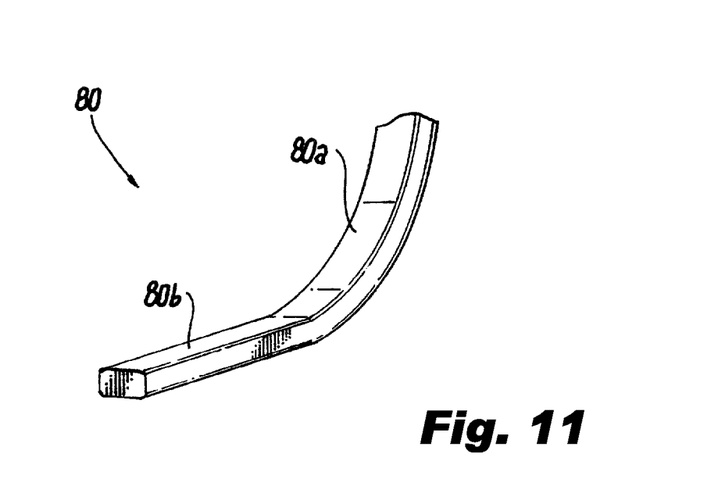
FIG. 11 is an enlarged localized perspective view of the distal end portion of the internal support wire shown in FIG. 10.

Referring now to FIGS. 10 and 11 in conjunction with FIG. 4, each of the splines 52a-52f of the basket assembly 50 has an internal support wire 80. Each support wire 80 is constructed from a shape memory alloy (e.g., Nitinol) and has an arcuate central portion 80a with distal and proximal leg portions 80b and 80c. The arcuate central portion 80a defines the curvature of each spline when the basket assembly 50 is in a radially outwardly spread condition. The distal leg portion 80b cooperates with another sprocket (similar to sprocket 60) in the end cap 58 at the distal end of the basket assembly 50 and the proximal leg portion 80c cooperates with the sprocket 60 in the open distal end portion of catheter shaft 18.

As best seen in FIG. 11, each internal support wire 80 preferably has a generally rectangular cross-section to prevent twisting and maintain radial alignment of the splines. The rectangular profile of each support wire 80 allows for angular alignment of all of the splines while still being flexible.

It should be understood that the irrigated basket-shaped mapping assembly of the catheter system 10 of the subject invention, can have any number of tubular splines. It can have four (4) tubular splines as illustrated in FIG. 6, it can have six (6) tubular splines as illustrated in FIG. 5, or it can have fewer than four splines and greater than six splines. It should be further understood by those having ordinary skill in the art, that each of the splines could have more than four (4) mapping electrodes or fewer than four (4) mapping electrodes. However, each spline preferably includes at least three (3) spaced apart generally cylindrical mapping electrodes thereon.

While the subject disclosure has been shown and described with reference to preferred embodiments, those skilled in the art will readily appreciate that changes or modifications may be made thereto without departing from the spirit or scope of the subject disclosure.

What is claimed is:

1. An intravascular catheter system comprising:
   a) a central housing having opposed proximal and distal portions;
   b) an elongated catheter shaft operatively associated with the distal portion of the housing, the catheter shaft having an elongated central support wire extending therethrough and a having an irrigated basket assembly operatively associated with a distal end portion thereof, the irrigated basket assembly having opposed proximal and distal portions and including a plurality of circumferentially arranged electrically insulated tubular splines each having a plurality of longitudinally spaced apart mapping electrodes thereon, wherein each mapping electrode has a raised circumferential outer surface for tissue contact, and wherein ramps are provided at opposed ends of each mapping electrode to provide a smooth transition between an outer surface of a tubular spline and the outer surface of the electrode;
   c) an elongated electrical conduit operatively associated with the housing and supporting a plurality of electrical conductors that extend through the catheter shaft and into the tubular splines of the irrigated basket assembly for communicating with the plurality of spaced apart mapping electrodes; and
   d) an elongated irrigation conduit operatively associated with the proximal portion of the housing, the irrigation conduit supporting an elongated irrigation lumen that extends through the catheter shaft and into the basket assembly and surrounds the central support wire so as to define an irrigation gap therebetween, wherein the irrigation lumen has an open distal end adjacent the distal portion of the basket assembly to allow for the egress of irrigation fluid from the irrigation gap, wherein an elongated cylindrical sprocket is provided within a distal end portion of the catheter shaft, adjacent to the proximal end portion of the basket assembly, with a number of circumferentially spaced apart radially outer grooves formed therein for maintaining the plurality of electrical conductors in a number of circumferentially spaced apart groups corresponding to the number of splines, wherein an arcuate spacer covers each spaced apart group of electrical conductors and maintains radial spacing between the conductors and an inner wall of the catheter shaft, and wherein each of the splines has an internal support wire having a generally rectangular cross-section to prevent twisting and maintain radial alignment of the splines, an arcuate central portion that defines a curvature of each spline when the basket assembly is in an outwardly spread condition, a proximal linear leg portion that cooperates with the sprocket provided in the distal end portion of the catheter shaft and a distal linear leg portion that cooperates with a second grooved cylindrical sprocket in an end cap at a distal end of the basket assembly, and wherein the proximal linear leg portion of each internal support wire is in contact with an outer surface of the sprocket provided within the distal end portion of the catheter shaft.

2. An intravascular catheter system as recited in claim 1, wherein the basket assembly is adapted and configured to transition between a first position in which the splines are compressed radially inwardly toward the central support wire for insertion and delivery and a second position in which the splines are spread radially outwardly away from the central support wire for physiological mapping.

3. An intravascular catheter system as recited in claim 1, wherein the basket assembly includes at least four circumferentially arranged splines.

4. An intravascular catheter system as recited in claim 3, wherein the basket assembly includes six circumferentially arranged splines.

5. An intravascular catheter system as recited in claim 1, wherein each internal support wire is constructed from a shape memory alloy.

6. An intravascular catheter system as recited in claim 1, wherein each of the circumferentially arranged splines has at least three spaced apart generally cylindrical mapping electrodes thereon.

7. An intravascular catheter system as recited in claim 1, wherein each of the mapping electrodes is constructed from an electrically conductive biocompatible material selected from the group consisting of platinum, platinum iridium alloy, MP35N and stainless steel.

8. An intravascular catheter system as recited in claim 1, wherein the sprocket provided within the distal end portion of the of the catheter shaft has a control bore extending therethrough for accommodating the central support wire and the irrigation lumen.

9. An intravascular catheter system as recited in claim 1, wherein the electrical conduit has an electrical connector operatively associated with a proximal end thereof for communicating with a power source.

10. An intravascular catheter system as recited in claim 1, wherein the irrigation lumen has at least one weeping hole adjacent the proximal portion of the basket assembly to allow for the egress of irrigation fluid from the irrigation gap.

11. An intravascular catheter system as recited in claim 1, wherein the irrigation conduit has an irrigation port assembly operatively associated with a proximal end portion thereof for communicating with a fluid source.

12. The intravascular catheter system as recited in claim 1, wherein each of the electrical conductors are free of contact with the sprocket provided within the distal end portion of the of the catheter shaft.

* * * * *